(12) United States Patent
Chen et al.

(10) Patent No.: US 8,551,020 B2
(45) Date of Patent: Oct. 8, 2013

(54) CROSSING GUIDEWIRE

(75) Inventors: Hancun Chen, Maple Grove, MN (US); Horng-Ban Lin, Maple Grove, MN (US); Pu Zhou, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 250 days.

(21) Appl. No.: 11/854,954

(22) Filed: Sep. 13, 2007

(65) Prior Publication Data

US 2008/0064989 A1 Mar. 13, 2008

Related U.S. Application Data

(60) Provisional application No. 60/825,540, filed on Sep. 13, 2006.

(51) Int. Cl.
*A61M 25/09* (2006.01)

(52) U.S. Cl.
USPC .............................. 600/585; 600/434; 600/435

(58) Field of Classification Search
USPC ......................................... 600/434, 435, 585
See application file for complete search history.

(56) References Cited

U.S. PATENT DOCUMENTS

| | | | |
|---|---|---|---|
| 1,553,227 A | 9/1925 | Feyk et al. | |
| 1,866,888 A | 7/1932 | Hawley | |
| 2,275,827 A | 3/1942 | Plensler | |
| 2,413,805 A | 1/1947 | Vickers | |
| 2,441,166 A | 5/1948 | Raspert | |
| 2,561,890 A | 7/1951 | Stoddard | |
| 2,722,614 A | 11/1955 | Fryklund | |
| 2,857,536 A | 10/1958 | Light | |
| 2,864,017 A | 12/1958 | Waltscheff | |
| 2,871,793 A | 2/1959 | Michie et al. | |
| 3,249,776 A | 5/1966 | Anderson et al. | |
| 3,322,984 A | 5/1967 | Anderson | |
| 3,334,253 A | 8/1967 | Hill | |
| 3,363,470 A | 1/1968 | Yavne | |
| 3,452,227 A | 6/1969 | Welch | |
| 3,452,742 A | 7/1969 | Muller | |
| 3,463,953 A | 8/1969 | Maxwell | |
| 3,512,019 A | 5/1970 | Durand | |
| 3,544,868 A | 12/1970 | Bates | |
| 3,625,200 A | 12/1971 | Muller | |

(Continued)

FOREIGN PATENT DOCUMENTS

| AU | 723040 | 12/1997 |
|---|---|---|
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Sean Dougherty
(74) *Attorney, Agent, or Firm* — Seager, Tufte & Wickhem, LLC

(57) ABSTRACT

Medical devices and methods for manufacturing and using medical devices. An example medical device includes a core member, a tubular member coupled to the core member, and a tip member coupled to the tubular member. The tubular member may have a plurality of slots formed therein. The tip member may include a polymeric material. An intermediate member may be disposed between the tubular member and the core member that aids the bonding of the tip member thereto.

18 Claims, 16 Drawing Sheets

(56) References Cited

U.S. PATENT DOCUMENTS

| | | |
|---|---|---|
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,425,723 A | 6/1995 | Wang |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |

| | | | | | | |
|---|---|---|---|---|---|---|
| 5,622,184 | A | 4/1997 | Ashby et al. | 6,203,485 | B1 | 3/2001 | Urick |
| 5,630,806 | A | 5/1997 | Inagaki et al. | RE37,148 | E | 4/2001 | Shank |
| 5,637,089 | A | 6/1997 | Abrams et al. | 6,214,042 | B1 | 4/2001 | Jacobsen et al. |
| 5,656,011 | A | 8/1997 | Uihlein et al. | 6,228,073 | B1 | 5/2001 | Noone et al. |
| 5,658,264 | A | 8/1997 | Samson et al. | 6,248,082 | B1 | 6/2001 | Jafari |
| 5,666,968 | A | 9/1997 | Imran et al. | 6,251,092 | B1 | 6/2001 | Qin et al. |
| 5,666,969 | A | 9/1997 | Urick et al. | 6,254,549 | B1 | 7/2001 | Ramzipoor |
| 5,669,926 | A | 9/1997 | Aust et al. | 6,260,458 | B1 | 7/2001 | Jacobsen et al. |
| 5,676,659 | A | 10/1997 | McGurk | 6,273,404 | B1 | 8/2001 | Holman et al. |
| 5,676,697 | A | 10/1997 | McDonald | 6,273,876 | B1 | 8/2001 | Klima et al. |
| 5,682,894 | A | 11/1997 | Orr et al. | 6,273,879 | B1 | 8/2001 | Keith et al. |
| 5,683,370 | A | 11/1997 | Luther et al. | 6,290,656 | B1 | 9/2001 | Boyle et al. |
| 5,690,120 | A | 11/1997 | Jacobsen et al. | 6,296,616 | B1 | 10/2001 | McMahon |
| 5,720,300 | A | 2/1998 | Fagan et al. | 6,296,631 | B2 | 10/2001 | Chow |
| 5,722,609 | A | 3/1998 | Murakami | 6,302,870 | B1 | 10/2001 | Jacobsen et al. |
| 5,728,063 | A | 3/1998 | Preissman et al. | 6,325,790 | B1 | 12/2001 | Trotta |
| 5,741,429 | A | 4/1998 | Donadio, III et al. | 6,338,725 | B1 | 1/2002 | Hermann et al. |
| 5,746,701 | A | 5/1998 | Noone | 6,346,091 | B1 | 2/2002 | Jacobsen et al. |
| 5,769,830 | A | 6/1998 | Parker | 6,352,515 | B1 | 3/2002 | Anderson et al. |
| 5,772,609 | A | 6/1998 | Nguyen et al. | 6,355,005 | B1 | 3/2002 | Powell et al. |
| 5,782,809 | A | 7/1998 | Umeno et al. | 6,355,027 | B1 | 3/2002 | Le et al. |
| 5,788,653 | A | 8/1998 | Lorenzo | 6,368,315 | B1 | 4/2002 | Gillis et al. |
| 5,788,654 | A | 8/1998 | Schwager | 6,368,316 | B1 | 4/2002 | Jansen et al. |
| 5,788,707 | A | 8/1998 | Del Toro et al. | 6,375,628 | B1 | 4/2002 | Zadno-Azizi et al. |
| 5,792,124 | A | 8/1998 | Horrigan et al. | 6,375,774 | B1 | 4/2002 | Lunn et al. |
| 5,797,856 | A | 8/1998 | Frisbie et al. | 6,379,369 | B1 | 4/2002 | Abrams et al. |
| 5,800,454 | A | 9/1998 | Jacobsen et al. | 6,390,993 | B1 | 5/2002 | Cornish et al. |
| 5,807,075 | A | 9/1998 | Jacobsen et al. | 6,398,758 | B1 | 6/2002 | Jacobsen et al. |
| 5,807,249 | A | 9/1998 | Qin et al. | 6,428,489 | B1 | 8/2002 | Jacobsen et al. |
| 5,810,885 | A | 9/1998 | Zinger | 6,428,512 | B1 | 8/2002 | Anderson et al. |
| 5,813,996 | A | 9/1998 | St. Germain et al. | 6,431,039 | B1 | 8/2002 | Jacobsen et al. |
| 5,827,225 | A | 10/1998 | Ma Schwab | 6,440,088 | B1 | 8/2002 | Jacobsen |
| 5,827,242 | A | 10/1998 | Follmer et al. | 6,478,778 | B1 | 11/2002 | Jacobsen et al. |
| 5,833,632 | A | 11/1998 | Jacobsen et al. | 6,488,637 | B1 | 12/2002 | Eder et al. |
| 5,836,926 | A | 11/1998 | Peterson et al. | 6,491,648 | B1 | 12/2002 | Cornish et al. |
| 5,843,050 | A | 12/1998 | Jones et al. | 6,491,671 | B1 | 12/2002 | Larson, III et al. |
| 5,843,244 | A | 12/1998 | Pelton et al. | 6,503,244 | B2 | 1/2003 | Hayman |
| 5,851,203 | A | 12/1998 | van Muiden | 6,508,803 | B1 | 1/2003 | Horikawa et al. |
| 5,895,378 | A | 4/1999 | Nita | 6,524,301 | B1 | 2/2003 | Wilson et al. |
| 5,897,537 | A | 4/1999 | Berg et al. | 6,530,934 | B1 | 3/2003 | Jacobsen et al. |
| 5,902,254 | A | 5/1999 | Magram | 6,547,779 | B2 | 4/2003 | Levine et al. |
| 5,902,290 | A | 5/1999 | Peacock, III et al. | 6,553,880 | B2 | 4/2003 | Jacobsen et al. |
| 5,904,657 | A | 5/1999 | Unsworth et al. | 6,556,873 | B1 | 4/2003 | Smits |
| 5,906,618 | A | 5/1999 | Larson, III | 6,579,246 | B2 | 6/2003 | Jacobsen et al. |
| 5,911,715 | A | 6/1999 | Berg et al. | 6,602,207 | B1 | 8/2003 | Mann et al. |
| 5,911,717 | A | 6/1999 | Jacobsen et al. | 6,602,280 | B2 | 8/2003 | Chobotov |
| 5,916,177 | A | 6/1999 | Schwager | 6,610,046 | B1 | 8/2003 | Usami et al. |
| 5,916,178 | A | 6/1999 | Noone | 6,623,448 | B2 | 9/2003 | Slater |
| 5,916,194 | A | 6/1999 | Jacobsen et al. | 6,636,758 | B2 | 10/2003 | Sanchez et al. |
| 5,931,830 | A | 8/1999 | Jacobsen et al. | 6,638,266 | B2 | 10/2003 | Wilson et al. |
| 5,935,108 | A | 8/1999 | Katoh et al. | 6,652,508 | B2 | 11/2003 | Griffin et al. |
| 5,947,940 | A | 9/1999 | Beisel | 6,682,493 | B2 | 1/2004 | Mirigian |
| 5,951,539 | A | 9/1999 | Nita et al. | 6,689,120 | B1 | 2/2004 | Gerdts |
| 5,957,842 | A * | 9/1999 | Littmann et al. ............ 600/381 | 6,702,762 | B2 | 3/2004 | Jafari et al. |
| 5,971,975 | A | 10/1999 | Mills et al. | 6,712,826 | B2 | 3/2004 | Lui |
| 5,980,471 | A | 11/1999 | Jafari | 6,730,095 | B2 | 5/2004 | Olson, Jr. et al. |
| 6,001,068 | A | 12/1999 | Uchino et al. | 6,749,560 | B1 | 6/2004 | Konstorum et al. |
| 6,004,279 | A | 12/1999 | Crowley et al. | 6,766,720 | B1 | 7/2004 | Jacobsen et al. |
| 6,014,919 | A | 1/2000 | Jacobsen et al. | 6,777,644 | B2 | 8/2004 | Peacock, III et al. |
| 6,017,319 | A | 1/2000 | Jacobsen et al. | 6,811,544 | B2 | 11/2004 | Schaer |
| 6,022,343 | A | 2/2000 | Johnson et al. | 6,837,898 | B2 | 1/2005 | Boyle et al. |
| 6,022,369 | A | 2/2000 | Jacobsen et al. | 6,866,642 | B2 | 3/2005 | Kellerman et al. |
| 6,024,730 | A | 2/2000 | Pagan | 6,887,235 | B2 | 5/2005 | O'Connor et al. |
| 6,027,461 | A | 2/2000 | Walker et al. | 6,918,882 | B2 | 7/2005 | Skujins et al. |
| 6,042,553 | A | 3/2000 | Solar et al. | 6,997,937 | B2 | 2/2006 | Jacobsen et al. |
| 6,045,547 | A | 4/2000 | Ren et al. | 7,001,369 | B2 | 2/2006 | Griffin et al. |
| 6,048,339 | A | 4/2000 | Zirps et al. | 7,074,197 | B2 | 7/2006 | Reynolds et al. |
| 6,056,702 | A | 5/2000 | Lorenzo | 7,153,277 | B2 | 12/2006 | Skujins et al. |
| 6,063,101 | A | 5/2000 | Jacobsen et al. | 7,182,735 | B2 | 2/2007 | Shireman et al. |
| 6,063,200 | A | 5/2000 | Jacobsen et al. | 7,494,687 | B2 * | 2/2009 | Cox ............... 427/2.24 |
| 6,066,361 | A | 5/2000 | Jacobsen et al. | 7,758,520 | B2 * | 7/2010 | Griffin et al. ......... 600/585 |
| 6,106,485 | A | 8/2000 | McMahon | 7,878,984 | B2 * | 2/2011 | Jacobsen et al. ..... 600/585 |
| 6,106,488 | A | 8/2000 | Fleming et al. | 7,989,042 | B2 * | 8/2011 | Obara et al. ......... 428/36.9 |
| 6,139,510 | A | 10/2000 | Palermo | 8,021,311 | B2 * | 9/2011 | Munoz et al. ........ 600/585 |
| 6,165,292 | A | 12/2000 | Abrams et al. | 8,257,279 | B2 * | 9/2012 | Davis et al. ......... 600/585 |
| 6,171,296 | B1 | 1/2001 | Chow | 2002/0013540 | A1 | 1/2002 | Jacobsen et al. |
| 6,183,410 | B1 | 2/2001 | Jacobsen et al. | 2002/0019599 | A1 | 2/2002 | Rooney et al. |
| 6,193,686 | B1 | 2/2001 | Estrada et al. | 2003/0009208 | A1 | 1/2003 | Snyder et al. |
| 6,197,014 | B1 | 3/2001 | Samson et al. | 2003/0060732 | A1 | 3/2003 | Jacobsen et al. |

| | | | | | | |
|---|---|---|---|---|---|---|
| 2003/0069522 A1 | 4/2003 | Jacobsen et al. | | JP | 4061840 | 2/1992 |
| 2003/0216668 A1 | 11/2003 | Howland et al. | | JP | 4099963 | 3/1992 |
| 2004/0111044 A1* | 6/2004 | Davis et al. | 600/585 | JP | 4213069 | 8/1992 |
| 2004/0116831 A1 | 6/2004 | Vrba | | JP | 4213070 | 8/1992 |
| 2004/0142643 A1 | 7/2004 | Miller et al. | | JP | 4236965 | 8/1992 |
| 2004/0167436 A1 | 8/2004 | Reynolds et al. | | JP | 5149969 | 6/1993 |
| 2004/0167437 A1 | 8/2004 | Sharrow et al. | | JP | 5-506806 | 10/1993 |
| 2004/0167441 A1 | 8/2004 | Reynolds et al. | | JP | 5506806 | 10/1993 |
| 2004/0181174 A2 | 9/2004 | Davis et al. | | JP | 5-309159 | 11/1993 |
| 2004/0181176 A1* | 9/2004 | Jafari et al. | 600/585 | JP | 5-507857 | 11/1993 |
| 2006/0121218 A1 | 6/2006 | Obara et al. | | JP | 6-501179 | 2/1994 |
| 2006/0122537 A1 | 6/2006 | Reynolds et al. | | JP | 631749 | 4/1994 |
| 2006/0189896 A1 | 8/2006 | Davis et al. | | JP | 6169996 | 6/1994 |
| 2006/0264904 A1 | 11/2006 | Kerby et al. | | JP | 6-63224 | 9/1994 |
| 2007/0100285 A1 | 5/2007 | Griffin et al. | | JP | 6312313 | 11/1994 |
| 2007/0100424 A1 | 5/2007 | Chew et al. | | JP | 728562 | 5/1995 |
| 2008/0021347 A1 | 1/2008 | Jacobsen et al. | | JP | 7124164 | 5/1995 |
| 2008/0021348 A1 | 1/2008 | Jacobsen et al. | | JP | 7124263 | 5/1995 |
| 2008/0021400 A1 | 1/2008 | Jacobsen et al. | | JP | 7136280 | 5/1995 |
| 2008/0021401 A1 | 1/2008 | Jacobsen et al. | | JP | 7148264 | 6/1995 |
| 2008/0021402 A1 | 1/2008 | Jacobsen et al. | | JP | 7505561 | 6/1995 |
| 2008/0021403 A1 | 1/2008 | Jacobsen et al. | | JP | 7037199 | 7/1995 |
| 2008/0021404 A1 | 1/2008 | Jacobsen et al. | | JP | 7185009 | 7/1995 |
| 2008/0021405 A1 | 1/2008 | Jacobsen et al. | | JP | 7255855 | 10/1995 |
| 2008/0021406 A1 | 1/2008 | Jacobsen et al. | | JP | 7275366 | 10/1995 |
| 2008/0021407 A1 | 1/2008 | Jacobsen et al. | | JP | 751067 | 11/1995 |
| 2008/0021408 A1 | 1/2008 | Jacobsen et al. | | JP | 8-229888 | 9/1996 |
| 2008/0077049 A1* | 3/2008 | Hirshman | 600/585 | JP | 8229888 | 9/1996 |
| 2008/0077119 A1 | 3/2008 | Snyder et al. | | JP | 8509141 | 10/1996 |
| 2008/0097247 A1* | 4/2008 | Eskuri | 600/585 | JP | 8317988 | 12/1996 |
| 2008/0097248 A1* | 4/2008 | Munoz et al. | 600/585 | JP | 9000164 | 4/1997 |
| | | | | JP | 9-276413 | 10/1997 |

FOREIGN PATENT DOCUMENTS

| | | | | | | |
|---|---|---|---|---|---|---|
| | | | | JP | 9276413 | 10/1997 |
| BR | PI 9712829 | 1/2000 | | JP | 9-294813 A | 11/1997 |
| CA | 2266685 | 5/2006 | | JP | 9294813 | 11/1997 |
| CA | 2255781 | 3/2007 | | JP | 10-118193 | 5/1998 |
| CN | 1230914 | 10/1999 | | JP | 10118193 | 5/1998 |
| DE | 2539191 | 3/1976 | | JP | 3325828 | 7/1998 |
| DE | 285514 | 12/1990 | | JP | 10305039 | 11/1998 |
| EP | 0 045 931 | 2/1982 | | JP | 10328191 | 12/1998 |
| EP | 0 069 522 | 1/1983 | | JP | 11226131 | 8/1999 |
| EP | 0 087 933 | 9/1983 | | JP | 11-267224 A | 10/1999 |
| EP | 0 111 044 | 6/1984 | | JP | 2000-197704 A | 7/2000 |
| EP | 0 181 174 | 5/1986 | | JP | 2000-510722 A | 8/2000 |
| EP | 0215173 | 3/1987 | | JP | 2000-511083 A | 8/2000 |
| EP | 0 377 453 | 7/1990 | | JP | 2001-500808 A | 1/2001 |
| EP | 0498476 A1 | 8/1992 | | JP | 3325828 | 7/2002 |
| EP | 0 565 065 | 6/1996 | | JP | 2002-529137 A | 9/2002 |
| EP | 0747089 A2 | 12/1996 | | JP | 2002-542901 A | 12/2002 |
| EP | 0 778 038 | 6/1997 | | JP | 2002-543896 A | 12/2002 |
| EP | 0 778 039 | 6/1997 | | JP | 2003-517893 A | 6/2003 |
| EP | 0 778 040 | 6/1997 | | JP | 3649604 | 2/2005 |
| EP | 0 812 599 | 12/1997 | | JP | 2005-534407 | 11/2005 |
| EP | 0 865 772 | 9/1998 | | SU | 712908 | 1/1980 |
| EP | 0 865 773 | 9/1998 | | SU | 758421 | 8/1980 |
| EP | 0 521 595 | 5/1999 | | SU | 1529365 | 12/1989 |
| EP | 0 917 885 | 5/1999 | | WO | WO 90/02520 | 3/1990 |
| EP | 0 937 481 | 8/1999 | | WO | WO 91/13364 | 9/1991 |
| EP | 0 790 066 | 4/2000 | | WO | WO 92/04072 | 3/1992 |
| EP | 0 608 853 | 4/2003 | | WO | WO 92/07619 | 5/1992 |
| EP | 0 935 947 | 12/2004 | | WO | WO 93/04722 | 3/1993 |
| EP | 0 934 141 | 11/2005 | | WO | WO 93/11313 | 6/1993 |
| GB | 2214354 | 8/1989 | | WO | 94/06500 A1 | 3/1994 |
| GB | 2257269 | 1/1993 | | WO | WO 95/24236 | 9/1995 |
| JP | 58-8522 | 1/1983 | | WO | WO 96/19255 | 6/1996 |
| JP | 60091858 | 5/1985 | | WO | 96/38193 | 12/1996 |
| JP | 61022752 | 1/1986 | | WO | WO 97/10022 | 3/1997 |
| JP | 62023361 | 1/1987 | | WO | WO 97/25914 | 7/1997 |
| JP | 62089470 | 4/1987 | | WO | WO 97/43949 | 11/1997 |
| JP | 62299277 | 12/1987 | | WO | WO 97/44083 | 11/1997 |
| JP | 6393516 | 4/1988 | | WO | WO 97/44086 | 11/1997 |
| JP | 63-181774 | 7/1988 | | WO | WO 98/10694 | 3/1998 |
| JP | 63217966 | 9/1988 | | WO | WO 99/04847 | 2/1999 |
| JP | 1089956 | 4/1989 | | WO | WO 99/11313 | 3/1999 |
| JP | 1135363 | 5/1989 | | WO | WO 00/27303 | 5/2000 |
| JP | 1158936 | 6/1989 | | WO | WO 00/30710 | 6/2000 |
| JP | 2107268 | 4/1990 | | WO | WO 00/48645 | 8/2000 |
| JP | 3081831 | 4/1991 | | WO | WO 00/57943 | 10/2000 |
| JP | 03-122850 | 12/1991 | | WO | WO 00/66199 | 11/2000 |

| | | | | | | |
|---|---|---|---|---|---|---|
| WO | WO 00/67845 | 11/2000 | | WO | WO 03/004086 | 1/2003 |
| WO | WO 00/72907 | 12/2000 | | WO | WO 03/008148 | 1/2003 |
| WO | WO 01/28620 | 4/2001 | | WO | 03/041783 | 5/2003 |
| WO | WO 01/36034 | 5/2001 | | WO | WO 2004/012804 | 2/2004 |
| WO | 0145912 | 6/2001 | | WO | 2004047899 | 6/2004 |
| WO | WO 01/45773 | 6/2001 | | WO | 2007/050718 | 5/2007 |
| WO | WO 01/93920 | 12/2001 | | WO | 2008/034010 | 3/2008 |
| WO | WO 02/13682 | 2/2002 | | | | |
| WO | WO 02/062540 | 8/2002 | | | | |

* cited by examiner

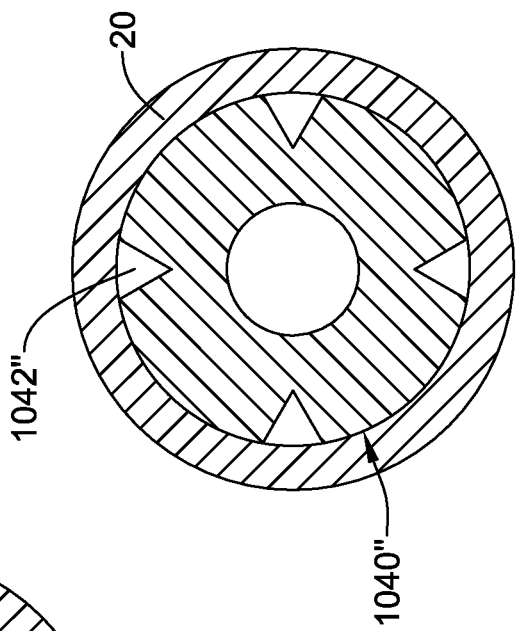
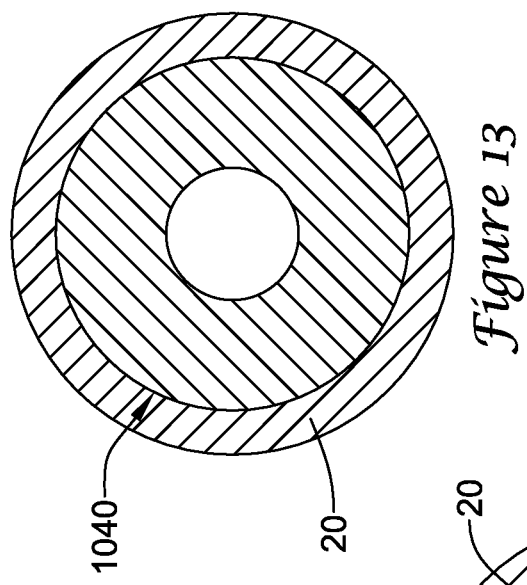
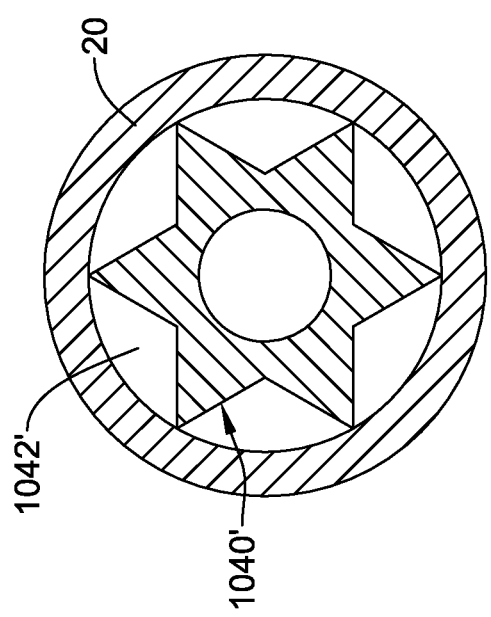

CROSSING GUIDEWIRE

CROSS REFERENCE TO RELATED APPLICATIONS

This application claims the benefit of priority to U.S. Provisional Application No. 60/825,540, filed Sep. 13, 2006, the entire disclosure of which is hereby incorporated by reference.

FIELD OF THE INVENTION

The present invention pertains to medical devices, and methods for manufacturing medical devices. More particularly, the present invention pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device includes a core member, a tubular member coupled to the core member, and a tip member coupled to the tubular member. The tubular member may have a plurality of slots formed therein. The tip member may include a polymeric material. An intermediate member may be disposed between the tubular member and the core member that aids the bonding of the tip member thereto.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 13 is a cross-sectional view depicting an insert disposed within a tubular member;

FIG. 14 is a cross-sectional view depicting an alternative insert disposed within a tubular member;

FIG. 15 is a cross-sectional view depicting an alternative insert disposed within a tubular member;

Figure 1:
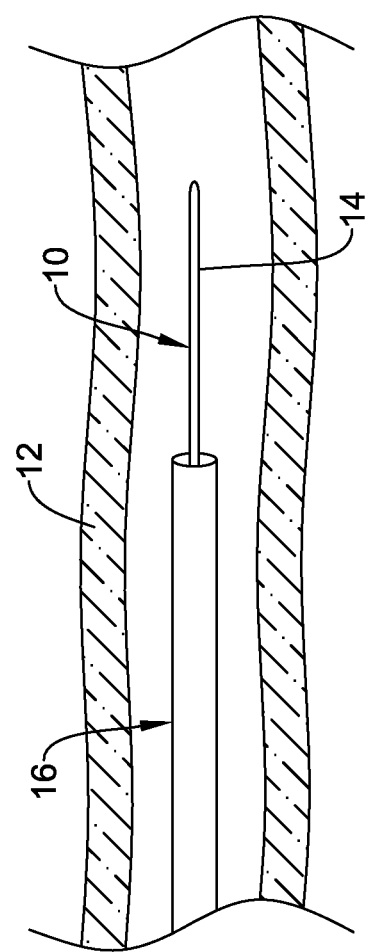
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an" and "the" include plural referents unless the content clearly dictates otherwise. As used in this specification and the appended claims, the term "or" is generally employed in its sense including "and/or" unless the content clearly dictates otherwise.

Weight percent, percent by weight, wt %, wt-%, % by weight, and the like are synonyms that refer to the concentration of a substance as the weight of that substance divided by the weight of the composition and multiplied by 100.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Although medical device 10 is depicted in several of the drawings as a guidewire, it is not intended to be limited to just being a guidewire. Indeed, medical device 10 may take the form of any suitable guiding, diagnosing, or treating device (including catheters, endoscopic instruments, laparoscopic instruments, etc., and the like) and it may be suitable for use at essentially any location and/or body lumen within a patient. For example, medical device/guidewire 10 may be suitable for use in neurological interventions, coronary interventions, peripheral interventions, etc. As such, guidewire 10 may be appropriately sized for any given intervention. For example, guidewire 10 may have an outside diameter of about 0.001 to 0.5 inches or about 0.0015 to 0.05 inches (e.g., about 0.010 to 0.014 inches) for neurological interventions; an outside diameter of about 0.001 to 0.5 inches or about 0.01 to 0.05 inches (e.g., about 0.014 inches) for coronary interventions; or an outside diameter of about 0.01 to 0.5 inches or about 0.02 to 0.05 inches (e.g., about 0.014-0.038 inches) for peripheral interventions. These dimensions, of course, may vary depending on, for example, the type of device (e.g., catheter, guidewire, etc.), the anatomy of the patient, and/or the goal of the intervention. In at least some embodiments, for example, guidewire 10 may be a crossing guidewire that can be used to help a clinician cross an occlusion or stenosis in vessel 12.

Figure 2:
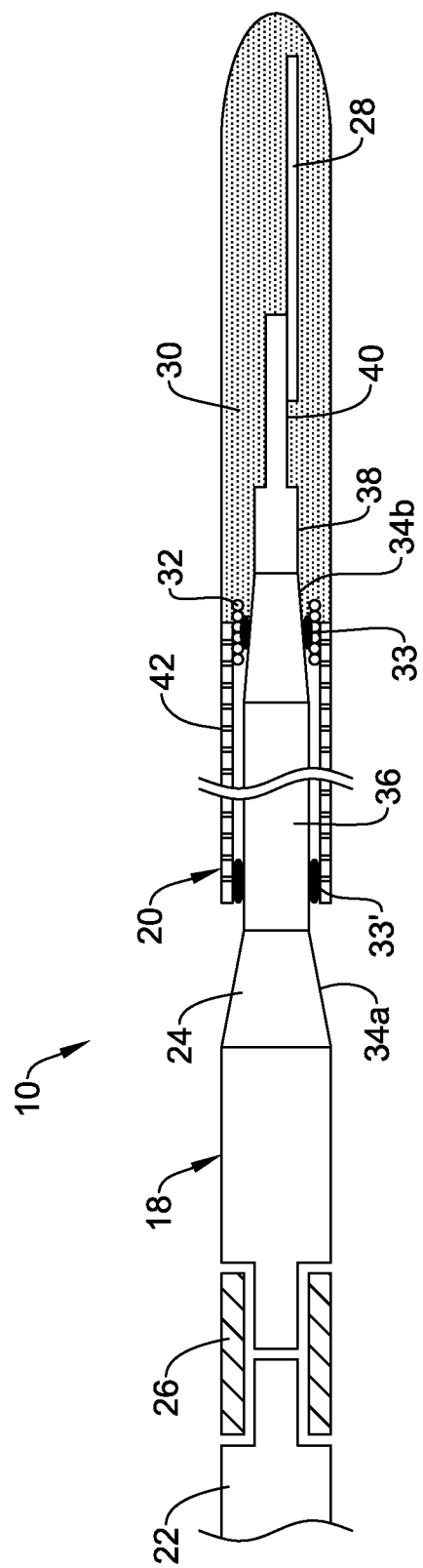
FIG. 2 is a partial cross-sectional view of an example medical device.

FIG. 2 is a partial cross-sectional view of guidewire 10. Here it can be seen that guidewire 10 may include a core member or core wire 18 and a tubular member 20 disposed over at least a portion of core wire 18. Core wire 18 may include a proximal section 22 and a distal section 24. A connector 26 may couple or otherwise attach proximal section 22 to distal section 24. Alternatively, core wire 18 may be a unitary member without a connector. A shaping member 28 may be coupled to core wire 18, for example distal section 24 of core wire 18, with a solder, adhesive, weld, braze, crimp, interlocking bond, mechanical bond, and the like, or any other suitable type of bond. To the extent applicable, it should be noted that any bond disclosed herein may generally include any of these types of bonds or any other suitable type of bond. Shaping member 28 may be made from a relatively inelastic material so that a clinician can bend or shape the distal end of guidewire 10 into a shape that may facilitate navigation of guidewire 10 through the anatomy. A tip member 30 may also be coupled to core wire 18 and/or tubular member 20 that defines an atraumatic distal tip of guidewire 10. In general, tip member 30 may include a polymeric material.

At least some embodiments of guidewire 10 are designed so that the various components thereof can be made from desirable materials (to impart desirable properties to guidewire 10), while still being joined together in a way that maintains the integrity of guidewire 10 during use. For example, core wire 18 and/or tubular member 20 may be made from a material that might add a desirable feature to guidewire 10. In addition, guidewire 10 may be designed so that abrupt flexibility changes can be reduced so that guidewire 10 is less likely to kink during use.

An intermediate member 32 may be may be disposed between tubular member 20 and core wire 18. In at least some embodiments, intermediate member 32 may be a coil. Coil 32 may extend distally beyond the distal end of tubular member 20 and bond with tip member 30, for example, in an interlocking manner. Some additional details of this interlocking bond are described below. Coil 32 may also bond to one of and/or both of tubular member 20 and/or core wire 18, for example, with a solder or adhesive bond 33 (or any of the other bonds described herein or any other suitable type of bond). In other words, coil 32 may be an "intermediate" or "joint" member that may overlap with both the distal portion of tubular member 20 and the proximal portion of tip member 30. This may help bond these structures and/or enhance the characteristics of the joint. Because of the various bonds achieved by coil 32, the overall integrity of guidewire 10 may be improved. Furthermore, coil 32 may also ease the transition (e.g., in flexibility) from tubular member 20 to tip member 30 (and/or the transition from core wire 18 to tip member 30) and help to reduce the likelihood that guidewire 10 may kink at the junction at tubular member 20 and tip member 30 (and/or the junction of core wire 18 and tip member 30).

In addition (or alternatively) to providing these features, coil 32 may also add additional desirable features. For example, coil 32 may include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result or bands and/or coils having a differing level of radiopacity than coil 32 may be included.

Coil 32 may also function to help center core wire 18 within tubular member 20. This may provide a direct line of contact between core wire 18 and tubular member 20 so that torque applied to core wire 18 (e.g., at proximal section 22) can be efficiently transferred to tubular member 20. This may allow a clinician to efficiently navigate guidewire 10 through the anatomy of a patient to a position adjacent an area of interest.

The various components of guidewire 10 may include a number of features, material compositions, and dimensions as well as variations on these characteristics. Below are listed some of these characteristics for illustration purposes. As will be appreciated, any values provided for dimensions herein are provided by way of example. Dimensions other than those provided below may be used without departing from the spirit of the invention.

Core wire 18 may have a length of about 9 to about 125 inches. Distal section 24 may make up about 5 to 80 inches of that total length, the remainder being derived from proximal section 22. In addition, core wire 18 may include a number of tapers or tapered regions (e.g., tapered regions 34a/34b). Tapered regions 34a/34b may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire 18 during the grinding process. In some embodiments, core wire 18 is centerless ground using a Royal Master HI-AC centerless grinder to define tapered regions 34a/34b.

Tapered region 34a may be about 0.5 to 5 inches or about 1 to 3 inches long while tapered region 34b may be about 0.5 to 10 inches or about 1 to 4 inches long. The outer diameter of core wire 18 may also vary. For example, the outer diameter of core wire 18 adjacent proximal section 22 may be about 0.005 to about 0.50 inches. The same or a different (e.g., smaller) outer diameter may be found at distal section 24. After transitioning through tapered region 34a, core wire 18 may have an outer diameter of about 0.001 to 0.05 inches or about 0.005 to 0.015 inches. Likewise, after transitioning through tapered region 34b, core wire 18 may have an outer diameter of about 0.0005 to 0.05 inches or about 0.001 to about 0.01 inches.

A generally constant outer diameter section 36 may extend between tapered regions 34a/34b. Section 36 may have a length of about 1 to 14 inches or about 2 to 8 inches. Located distal of tapered region 34b is a shoulder or narrowed region 38 that may be narrowed abruptly (as shown) or more gently using any of the appropriate technique or methods described herein or any other suitable method. A portion 40 of narrowed region 38 may be flattened or otherwise further narrowed (e.g., abruptly or gently). Narrowed region 38 may have a length of about 0.01 to 1 inches or about 0.05 to 0.25 inches and an outer diameter of about 0.001 to about 0.05 inches or about 0.001 to 0.005 inches. Portion 40 may have a length of about 0.01 to 0.25 inches or about 0.01 to about 0.1 inches and an outer diameter of about 0.001 to about 0.05 inches or about 0.001 to 0.005 inches.

Core wire 18 can have a solid cross-section, but in some embodiments, can have a hollow cross-section. In yet other embodiments, core wire 18 can include a combination of areas having solid cross-sections and hollow cross sections. Moreover, core wire 18, or portions thereof, can be made of rounded wire, flattened ribbon, or other such structures having various cross-sectional geometries. The cross-sectional geometries along the length of core wire 18 can also be constant or can vary. For example, FIG. 2 depicts core wire 18 as having a round cross-sectional shape. It can be appreciated that other cross-sectional shapes or combinations of shapes may be utilized without departing from the spirit of the invention. For example, the cross-sectional shape of core wire 18 may be oval, rectangular, square, polygonal, and the like, or any suitable shape.

Shaping member 28 may be bound, for example with solder, adhesive, or in any other manner to portion 40 in an overlapping bond. For example, about 0.01 to 0.10 inches or about 0.01 to 0.05 inches of shaping member 28 may overlap with the end of portion 40. Shaping member 28 itself may have a length of about 0.01 to 1 inches or about 0.25 to 1 inches. At least some embodiments of shaping member 28 are non-circular (e.g., ribbon-shaped) and may have dimensions of about 0.001 to 0.01 inches or about 0.001 to 0.005 by about 0.002 to 0.01 inches or 0.002 to 0.007 inches.

It should be noted that some embodiments of guidewire 10 are contemplated that do not include a shaping member 28. In these embodiments, for example, core wire 18 may extend into a substantial portion or substantially the length of tip member 30. In such embodiments of core wire 18, a section of core wire 18, for example within tip member 30, may be flattened or otherwise narrowed. This flattening or narrowing, for example, may be near the distal end of core wire 18. Embodiments of guidewire 10 that do not include a shaping member 28 are contemplated that can either lack (i.e., core wire 18 is a unitary member) or include connector 26.

Tubular member 20 may be bonded using any suitable technique to core wire 18. For example, tubular member 20 may be bonded to core wire 18 and coil 32 at solder bond 33 (which may alternatively be any of the other bonds described herein or any other suitable type of bond). Indeed, portions or all of core wire 18 may include a solder coating that facilitates the joining of core wire 18 to other structures such as tubular member 20. At the proximal end of tubular member 20, tubular member 20 may also be bonded to core wire 18 using any suitable technique such as a laser bond 33' (which may alternatively be any of the other bonds described herein or any other suitable type of bond). Essentially any suitable bonding technique (including those described herein) may be used without departing from the spirit of the invention.

In at least some embodiments, tubular member 20 includes a plurality of cuts, apertures, and/or slots 42 formed therein. Slots 42 can be formed by methods such as micro-machining, saw-cutting (e.g., using a diamond grit embedded semiconductor dicing blade), laser cutting, electron discharge machining, grinding, milling, casting, molding, chemically etching or treating, or other known methods, and the like. In some such embodiments, the structure of the tubular member 20 is formed by cutting and/or removing portions of the tube to form slots 42. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 42 in tubular member 20 using any of these or other manufacturing steps.

Various embodiments of arrangements and configurations of slots 42 are contemplated. In some embodiments, at least some, if not all of slots 42 are disposed at the same or a similar angle with respect to the longitudinal axis of the tubular member 20. As shown, slots 42 can be disposed at an angle that is perpendicular, or substantially perpendicular, and/or can be characterized as being disposed in a plane that is normal to the longitudinal axis of tubular member 20. However, in other embodiments, slots 42 can be disposed at an angle that is not perpendicular, and/or can be characterized as being disposed in a plane that is not normal to the longitudinal axis of tubular member 20. Additionally, a group of one or more slots 42 may be disposed at different angles relative to another group of one or more slots 42. The distribution and/or configuration of slots 42 can also include, to the extent applicable, any of those disclosed in U.S. Pat. Publication No. US 2004/0181174, the entire disclosure of which is herein incorporated by reference.

Slots 42 may be provided to enhance the flexibility of tubular member 20 while still allowing for suitable torque transmission characteristics. Slots 42 may be formed such that one or more rings and/or turns interconnected by one or more segments and/or beams are formed in tubular member 20, and such rings and beams may include portions of tubular member 20 that remain after slots 42 are formed in the body of tubular member 20. Such an interconnected ring structure may act to maintain a relatively high degree of torsional stiffness, while maintaining a desired level of lateral flexibility. In some embodiments, some adjacent slots 42 can be formed such that they include portions that overlap with each other about the circumference of tubular member 20. In other embodiments, some adjacent slots 42 can be disposed such that they do not necessarily overlap with each other, but are disposed in a pattern that provides the desired degree of lateral flexibility.

Additionally, slots 42 can be arranged along the length of, or about the circumference of, tubular member 20 to achieve desired properties. For example, adjacent slots 42, or groups of slots 42, can be arranged in a symmetrical pattern, such as being disposed essentially equally on opposite sides about the circumference of tubular member 20, or can be rotated by an angle relative to each other about the axis of tubular member 20. Additionally, adjacent slots 42, or groups of slots 42, may be equally spaced along the length of tubular member 20, or can be arranged in an increasing or decreasing density pattern, or can be arranged in a non-symmetric or irregular pattern. Other characteristics, such as slot size, slot shape and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section 26, or a distal section 28, or the entire tubular member 20, may not include any such slots 42.

As suggested above, slots 42 may be formed in groups of two, three, four, five, or more slots 42, which may be located at substantially the same location along the axis of tubular member 20. Within the groups of slots 42, there may be included slots 42 that are equal in size (i.e., span the same circumferential distance around tubular member 20). In some of these as well as other embodiments, at least some slots 42 in a group are unequal in size (i.e., span a different circumferential distance around tubular member 20). Longitudinally adjacent groups of slots 42 may have the same or different configurations. For example, some embodiments of tubular member 20 include slots 42 that are equal in size in a first group and then unequally sized in an adjacent group. It can be appreciated that in groups that have two slots 42 that are equal in size, the beams (i.e., the portion of tubular member 20 remaining after slots 42 are formed therein) are aligned with the center of tubular member 20. Conversely, in groups that have two slots 42 that are unequal in size, the beams are offset from the center of tubular member 20. Some embodiments of tubular member 20 include only slots 42 that are aligned with the center of tubular member 20, only slots 42 that are offset from the center of tubular member 20, or slots 42 that are aligned with the center of tubular member 20 in a first group and offset from the center of tubular member 20 in another group. The amount of offset may vary depending on the depth (or length) of slots 42 and can include essentially any suitable distance.

The materials that can be used for the various components of guidewire 10 may include those commonly associated with medical devices. For example, core wire 18, and/or tubular member 20, and/or connector 26, and/or coil 32, and/or shaping member 28, and/or tip member 28, and the like may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL™ 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material including those material listed above.

In some embodiments, a degree of MRI compatibility is imparted into guidewire 10. For example, to enhance compatibility with Magnetic Resonance Imaging (MRI) machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using any suitable connecting techniques and/or with connector 26. For example, the different portions of core wire 18 can be connected using welding (including laser welding), soldering, brazing, adhesive, or the like, or combinations thereof. These techniques can be utilized regardless of whether or not connector 26 is utilized. Connector 26 may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connector 26 including those connectors described in U.S. Pat. Nos. 6,918,882 and 7,071,197 and/or in U.S. Patent Pub. No. US 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18 and/or tubular member, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of tip member 30. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Coil 32, as indicated above, may be made from a radiopaque material such as platinum or any of the other radiopaque materials disclosed herein. In at least some embodiments, the wire used to define coil 32 has a generally round cross-sectional shape and a diameter of about 0.0001 to 0.05 inches or about 0.001 to 0.005 inches and is wound so as to have a pitch of about 0.0005 to 0.01 inches or about 0.001 to about 0.005 inches. This configuration, however, is not intended to be limiting as coils having a non-circular cross-sectional shape are contemplated including those with essentially any appropriate dimensions.

Figure 3:
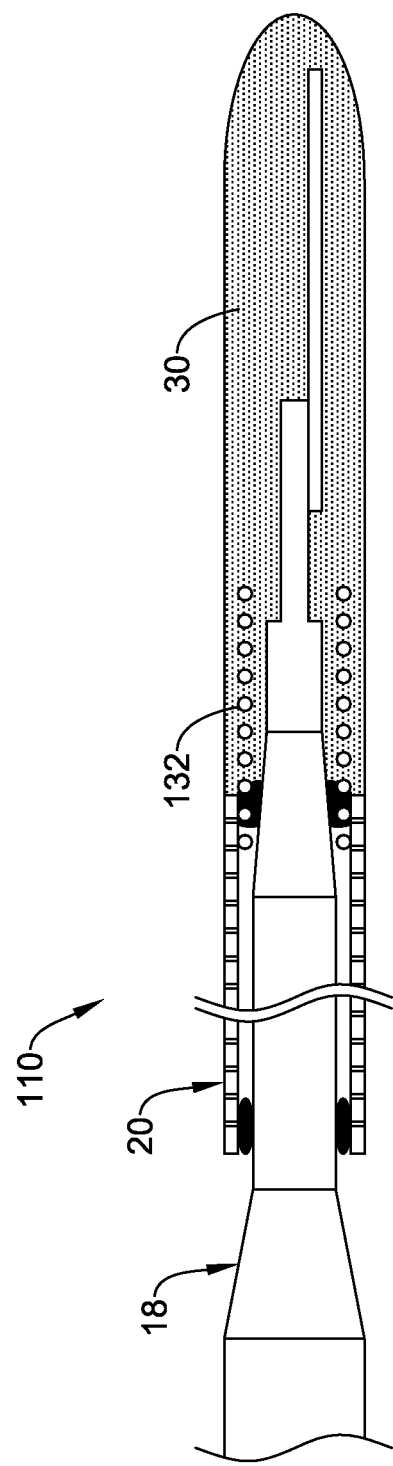
FIG. 3 is a partial cross-sectional view of another example medical device.

As indicated above, coil 32 may, for example, improve the bond and ease the transition between tubular member 20 and tip member 30 as well as between core wire 18 and tip member 30. This may be because coil 32 may be bonded to tubular member 20, core wire 18, or both and coil 32 may also be bonded to tip member 30 and because coil 32 may overlap with and extend distally beyond tubular member 20. The bond between coil 32 and tip member 30 may be an interlocking bond that further enhances the overall integrity of guidewire 10 adjacent to tip member 30. The interlocking bond may be formed by tip member 30 being disposed between adjacent windings of coil 32. In some example guidewires, such as guidewire 110 (which is otherwise similar in form and function to guidewire 10) depicted in FIG. 3, coil 132 (which is otherwise similar to coil 32) is wound to have an even more open pitch than 32 to further facilitate this bond and the interlocking nature thereof.

Figure 4:
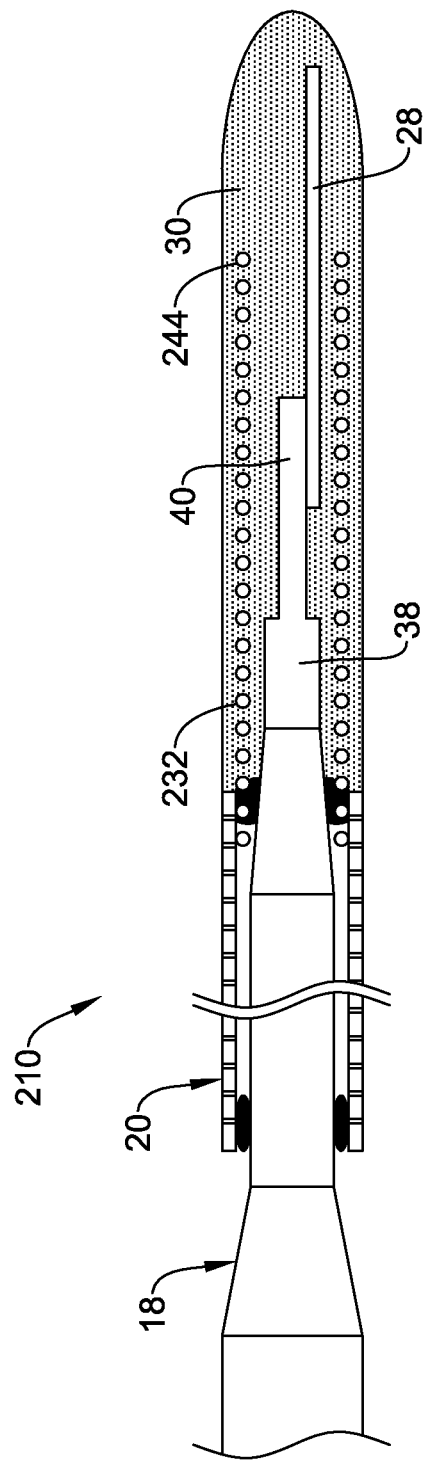
FIG. 4 is a partial cross-sectional view of another example medical device.

FIG. 4 depicts another example guidewire 210, which may be in some respects similar in form and function to other guidewires disclosed herein, that illustrates that coil 232 (similar to other coils disclosed herein) may have a distal end 244 that extends further into tip member 30. For example, distal end 244 may extend beyond narrowed region 38, and/or beyond portion 40, and/or beyond the intersection of portion 40 and shaping member 28. Of course, the precise location for distal end 244 of coil 232 can vary and may include essentially any suitable location. Extending the length of coil 232 may desirably impact the bond between tip member 30 and coil 232 by allowing the bond to be effectuated over a greater portion of the length of tip member 30 (and guidewire 210).

In addition to variations to coil 32/132/232, tip member 30 may also vary. Generally, tip member 30 may include a polymer including any of those listed herein. In some of these as well as other embodiments, tip member includes a radiopaque material. For example, tip member 30 or discrete portions thereof may include about 50-95 wt-% or about 75-95 wt-% radiopaque material with the balance being polymeric. In other words, tip member 30 may include a polymer loaded with radiopaque material. In some embodiments, the radiopaque material includes tungsten and the polymeric material includes polyurethane.

As indicated above, tip member 30 may be disposed over a portion of core wire 18, thereby bonding with and encapsulating that portion of core wire 18 therein. Tip member 30 may also be disposed over shaping member 28, thereby bonding with and encapsulating shaping member 28 therein.

Figure 2A:
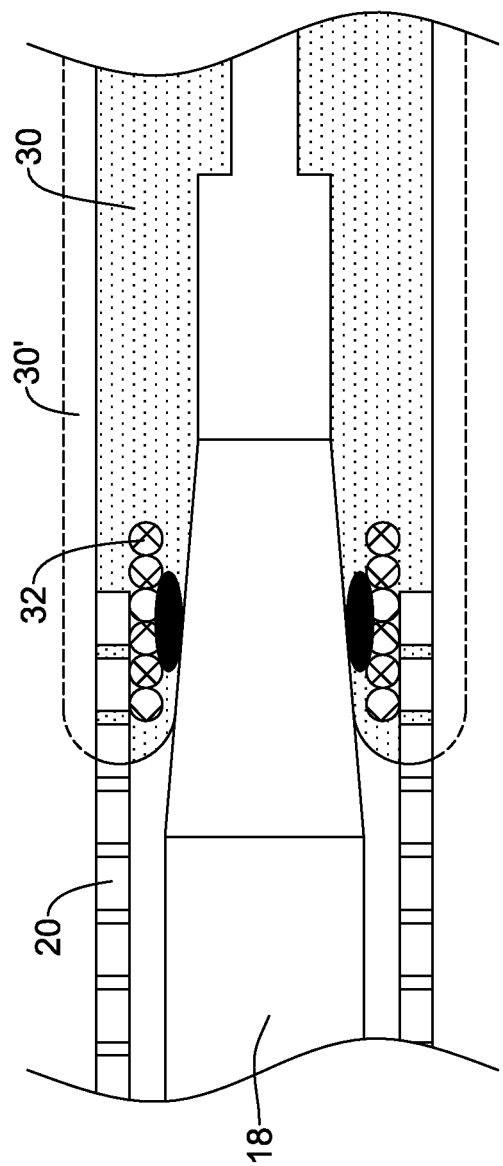
FIG. 2A is a partial cross-sectional view of a portion of an example medical device that depicts at least some of the method for manufacturing the device.

Turning back now to FIG. 2 and to FIG. 2A, in some embodiments, tip member 30 may abut and bond with tubular member 20. In other embodiments, tip member 30 may be disposed over (i.e., along the exterior) and/or under (i.e., along the interior) tubular member 20 along at least a portion of the length of tubular member 20 as seen in FIG. 2A. This may occur as part of the manufacturing process that produces guidewire 10 (or other guidewires disclosed herein) or a subassembly of guidewire 10 (or others). Disposing tip member over and/or under tubular member 20 may also result in some of tip member 30 being disposed in slots 42. In some of these embodiments, portions or all of the tip member 30 disposed over and/or under tubular member 20, for example portion 30' (shown in phantom), may be removed during manufacture of guidewire 10 (or other guidewires disclosed herein).

It can be appreciated that in order to create the interlocking bond between coil 32/132/232 and tip member 30, tip member 30 may be added to guidewire 10 after a guidewire subassembly is manufactured that includes coil 32/132/232 extending distally from tubular member 20. At this point, tip member 30 may be disposed over the appropriate portions of core wire 18, coil 32/132/232, and/or tubular member 20. This may include disposing tip member 30 (e.g., in the form of a tube) over the appropriate structures and then bonding tip member 30 via a reflow process. In addition, a heat shrink tube may be disposed over tip member 30 to facilitate this process. Subsequently, tip member may be ground, heated/molded, or otherwise finished so as to have the appropriate shape, texture, feel, etc. In other embodiments, coating, dipping, molding, casting, extrusion, or the like may be used in addition to or as an alternative to a reflow process.

Figure 5:
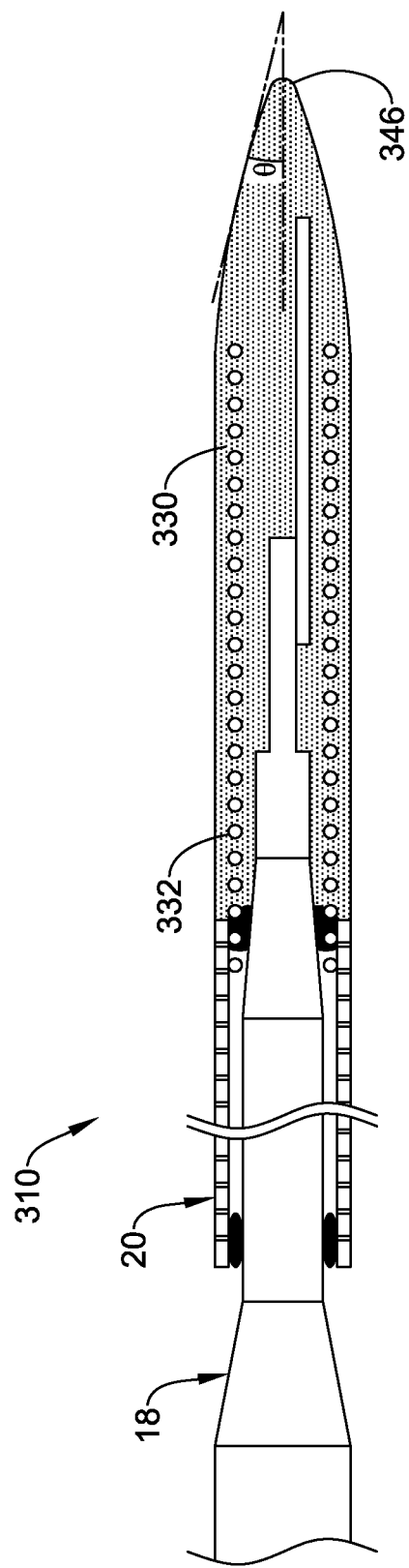
FIG. 5 is a partial cross-sectional view of another example medical device.

The shape of tip member 30, particularly at the distal end of guidewire 10, can vary. For example, the shape of tip member 30 as depicted in FIG. 2 can be described as being rounded, bullet-shaped, etc. However, the precise shape can vary. For example, FIG. 5 depicts guidewire 310 (which includes coil 332 that may be similar to any of the other coils described herein) where tip member 330 has a slightly more pointed distal end 346. Indeed, an angle θ is defined between the longitudinal axis of core wire 18 and the exterior profile of tip member 330 at distal end 346. Angle θ may be less than about 60°, or less than about 45°, or less than about 30°, or less than about 15°. Different angles may be selected for particular interventions such as to allow guidewire 10/110/210/310 to more effectively achieve its intended purpose.

Figure 6:
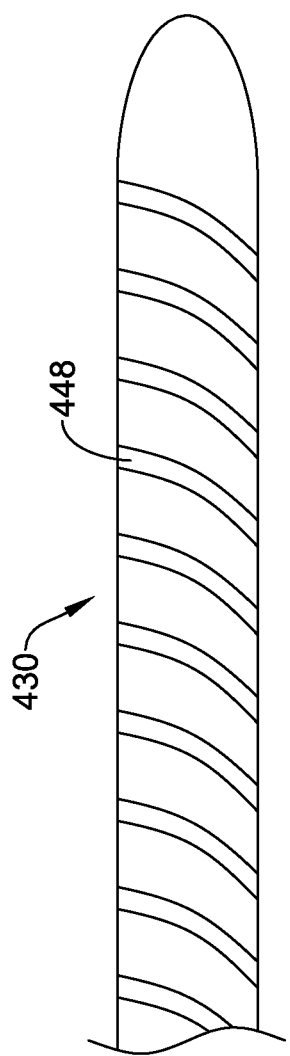
FIG. 6 is a partial cross-sectional view of another example medical device.

FIG. 6 depicts an alternative tip member 430 that has a structural feature 448 defined therein. Feature 448 may take a number of different forms such as that of a thread, groove, series of slots or perforations, score, combinations thereof, and the like, etc. that is defined within a portion of tip member 430. This may further enhance the ability of a guidewire (including any of those disclosed herein) to perform its intended purpose. For example, if feature 448 includes a thread or groove, the thread or groove may improve the ability of a guidewire (e.g., a crossing guidewire) intended for use in crossing an occlusion such as a stenosis. For example, such a groove or thread may improve the anchorability of the guidewire in the vessel when attempting to cross an occlusion and/or stenosis. In some embodiments, a groove or thread may additionally or alternatively aid in engaging and/or pulling the guidewire through an occlusion when rotated or provide additional features. Feature 448 may also provide desired flexibility characteristics. Numerous variations are contemplated along this theme and such variations are within the scope and spirit of the invention.

Figure 7:
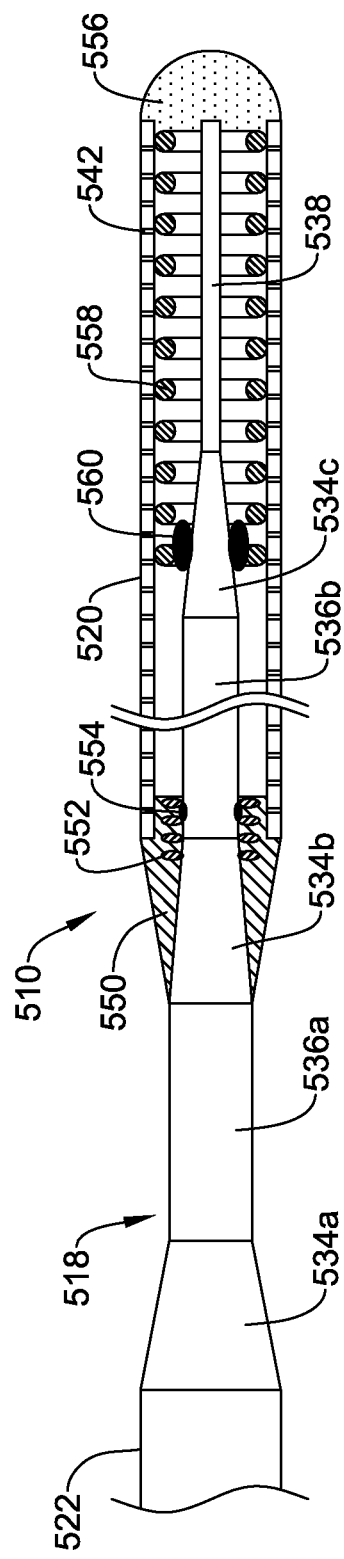
FIG. 7 is a partial cross-sectional view of another example medical device.

FIG. 7 illustrates another example guidewire 510 that may be similar in similar in some respects to others described herein. Guidewire 510 includes core wire 518 having a proximal section 522, tapered regions 534a/534b/534c, intermediate regions 536a/536b, and narrowed region 538. Core wire 518 is similar to other core wires disclosed herein except for the arrangement of regions 534a/534b/534c/536a/536b/538 and that, in at least some embodiments, core wire 518 is made of a singular material. For example, core wire 518 may be made of stainless steel, nickel-titanium alloy, or any other suitable material.

The dimension of guidewire 510 (e.g., the outer diameter of guidewire 510) may be similar to those of other guidewires disclosed herein (e.g., the outer diameter of other guidewires). The dimensions of core wire 518 may be generally similar to those of core wire 18. For example, tapered region 534a may have a length of about 0.5 to 5 inches or about 1 to 3 inches. Intermediate region 536a, which is disposed adjacent to tapered region 534a, may have an outer diameter of about 0.001 to 0.5 inches or about 0.001 to 0.01 inches and a length of about 1 to 25 inches or about 1 to 10 inches. Tapered region 534b may have a length of about 0.1 to 2 inches or about 0.25 to 2 inches. Intermediate region 536b, which is disposed adjacent to tapered region 534b, may have an outer diameter of about 0.001 to 0.1 inches or about 0.001 to 0.01 inches and a length of about 1 to 25 inches or about 1 to 10 inches. Tapered region 534c may have a length of about 0.5 to 5 inches or about 1 to 5 inches. Narrowed region 538, which is disposed adjacent to tapered region 534c, may have an outer diameter of about 0.001 to 0.1 inches or about 0.001 to 0.01 inches and a length of about 1 to 25 inches or about 1 to 10 inches.

Tubular member 520 may be generally similar to tubular member 20 in form and function and may include slots 542 formed therein. At its proximal end, tubular member 520 is attached to core wire 518, for example, with a solder, adhesive, or other suitable bond 550. Adjacent bond 550 may be a coil 552 that may function, for example, to aid in securing tubular member 520 to core wire 518. Coil 552 may also include a radiopaque material so as to aid in the visualization of guidewire 510. In at least some embodiments, coil 552 is bonded to core wire 518 with, for example, a laser or other suitable bond 554. At the distal end of tubular member 520 is a solder ball distal tip 556 that is also bonded to core wire 518.

Another coil 558 may be disposed within tubular member 520. Coil 558 may include a radiopaque material and may be secured to core wire 518 via a solder or any other suitable bond 560.

Figure 8:
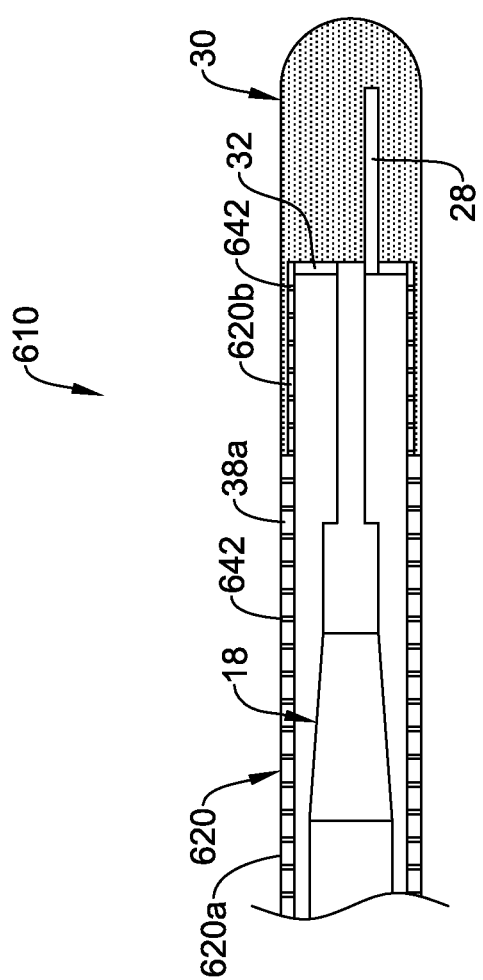
FIG. 8 is a partial cross-sectional view of an example medical device.

FIG. 8 is a partial cross-sectional view of guidewire 610 that may be similar in form and function to any of the other guidewires disclosed herein except that tubular member 620 may include a first section 620a and a second section 620b. With this arrangement, a portion of tubular member 620 (or other tubular members disclosed herein), for example second section 620b, may function as an intermediate member like coil 32 or other structures described herein and, consequently, it may provide a number of desirable features to guidewire 610. In some embodiments, first section 620a and second section 620b are defined by discrete, separate tubes that are bonded together to define tubular member 620. In other embodiments, first section 620a and second section 620b are both part of the same, singular, tubular member 620 (e.g., tubular member 620 is made from a single monolith of material). In these later embodiments, first section 620a and second section 620b may be distinguished from one another by physical location, size or shape, or in some other manner.

In at least some embodiments, the outer diameters of sections 620a/620b are different. The different outer diameters may be created, for example, by grinding away a portion of tubular member 620. In some embodiments, the outer diameter of second section 620b may be smaller than the outer diameter of first section 620a. This arrangement, in embodiments where second section 620b is disposed distally of first section 620a, creates a general decrease in the outer diameter of tubular member 620 in the distal direction. However, other embodiments are contemplated that have different configurations such as where second section 620b may have a larger outer diameter than first section 620a. Indeed, some embodiments are contemplated where first section 620a, second section 620b, or both may have varying outer diameters (e.g., they are tapered or otherwise include multiple regions having different outer diameters) so that a practical size comparison is only appropriate when particular and/or discrete area of sections 620a/620b are identified for comparison. In some of these as well as other embodiments, sections 620a/620b may have the same or a different wall thickness relative to one another. For example, section 620a may have a "thicker" wall than section 620b. However, the opposite may also be true.

The use of a multi-sectioned tubular member 620 in guidewire 610 may provide a number of desirable features. For example, in embodiments where first section 620a may have a larger outer diameter than second section 620b, the transition from the outer diameter of first section 620a to the outer diameter of second section 20b may provide a generally smooth transition in flexibility. In addition, in embodiments where first section 620a is located proximally of second section 620b, this configuration may provide for a smooth transition in flexibility from the proximal (e.g., more stiff) end to the distal (e.g., more flexible) end of guidewire 10. This may reduce the likelihood of kinking in guidewire 610 because abrupt changes in flexibility may be avoided or otherwise reduced.

Multi-sectioned tubular member 620 may also improve the bond between tubular member 620, core wire 18, and tip member 30. This may be because tip member 30 may overlap with tubular member 620, for example, along second section 620b. This may increase the surface area of contact between tip member 30 and tubular member 620. Furthermore, the overlapping arrangement of tubular member 620 and tip member 30 may allow forces (e.g., torque) that are applied to tubular member 620 to more efficiently transfer to tip member 30. Of course, a number of additional benefits may also be achieved through the use of tubular member 620.

In some embodiments, slots 642, which may have an arrangement and/or configuration similar to slots 42 described above, may be arranged in substantially the same way for both first section 620a and second section 620b of tubular member 620. However, this need not be the case. For example, slots 642 or groups of slots 642 may be longitudinally spaced apart from one another differing distances depending on which section 620a/620b of tubular member 620 they are in. In some embodiments, slots 642 are longitudinally spaced a greater distance in first section 620a than in second section 620b. Indeed, in some embodiments, portions or all of either first section 620a, second section 620b, or both may lack slots 642. Numerous other arrangements are contemplated that take advantage of the various slot arrangements and/or configurations discussed above.

Figure 9:
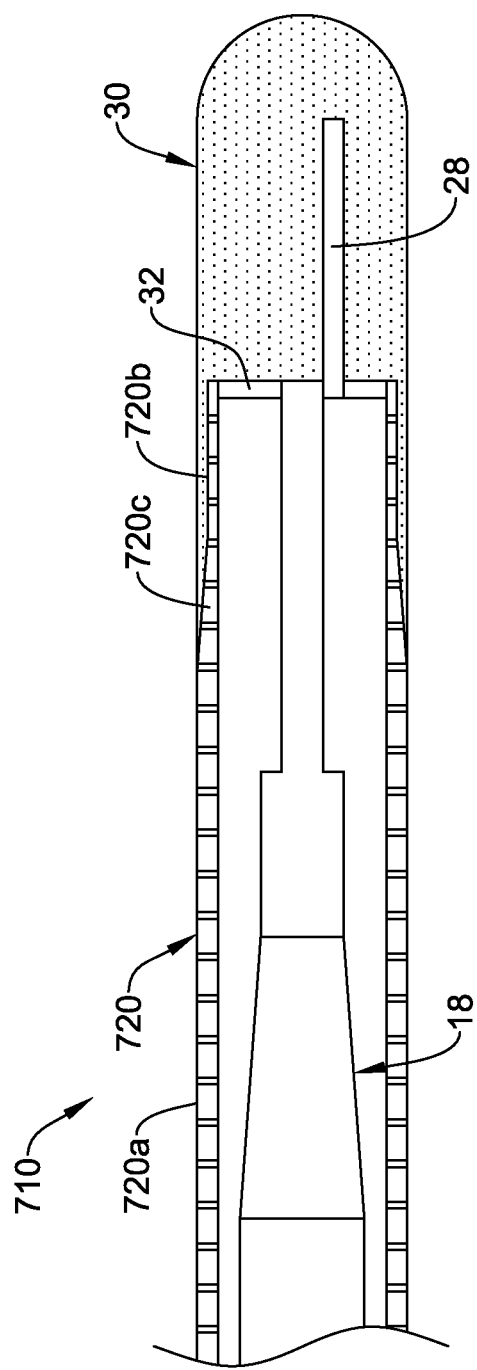
FIG. 9 is a partial cross-sectional view of another example medical device.

Tubular member 620, as depicted in FIG. 8, shows a step-like change in outer diameter between first section 620a and second section 620b. Other embodiments are contemplated, however, with a different arrangement. For example, FIG. 9 depicts another example guidewire 710 that may be similar to guidewire 610 or other guidewires disclosed herein except for that slotted tubular member 720 gradually tapers from first section 720a to second section 720b. This tapering may occur across a tapered section 720c of tubular member 720. This arrangement and/or configuration of tubular member 720 may help to ease the transition in flexibility from the proximal end to the distal end of tubular member 720 and/or of guidewire 710. This may reduce or eliminate abrupt changes in flexibility, which may help to reduce the likelihood of kinking in guidewire 710.

Figure 10:
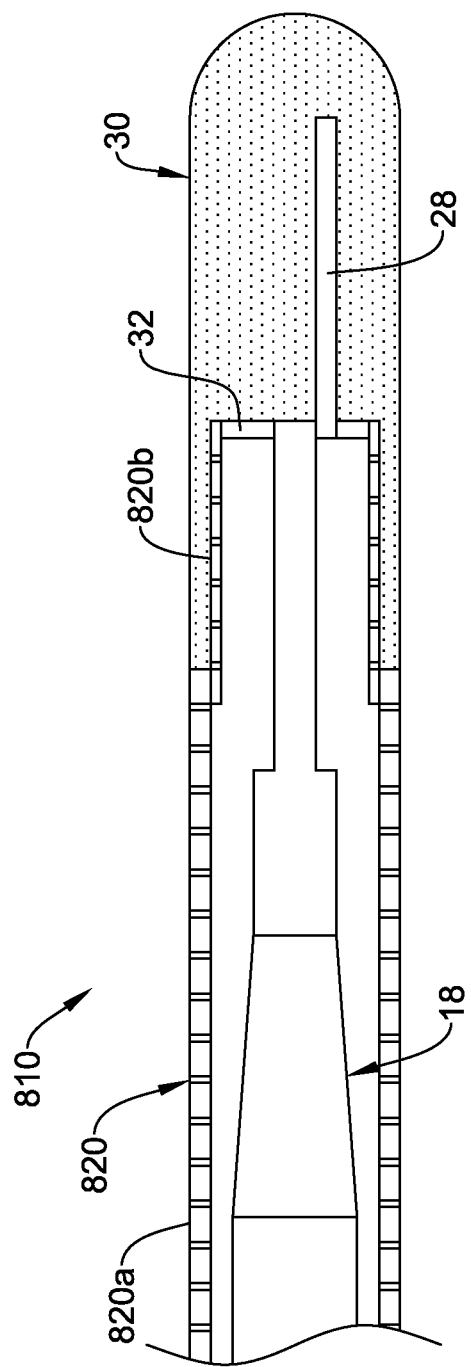
FIG. 10 is a partial cross-sectional view of another example medical device.

FIG. 10 depicts another guidewire 810 (that may be otherwise similar to other guidewires disclosed herein) with an alternative slotted tubular member 820. Tubular member 820 includes first section 820a and second section 820b that are arranged in an overlapping manner. This arrangement may also help to create a smooth transition in flexibility from the proximal end to the distal end of tubular member 820 and/or guidewire 810 as well as desirably reduce the likelihood of kinking.

Figure 11:
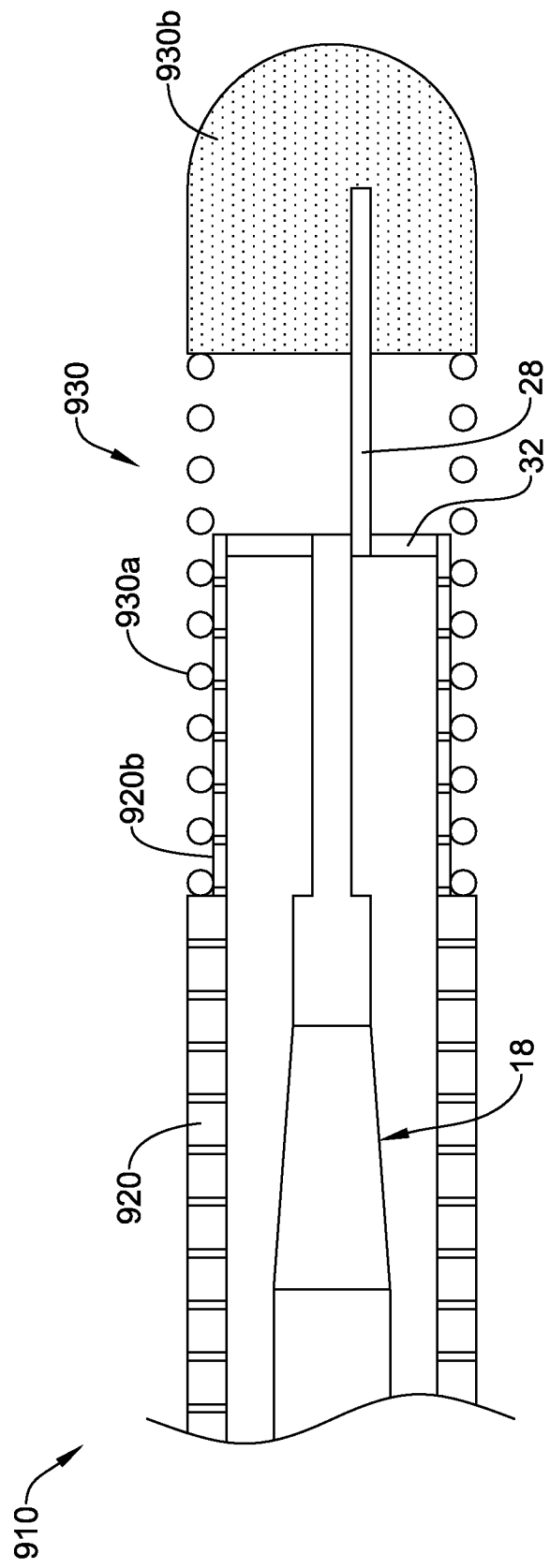
FIG. 11 is a partial cross-sectional view of another example medical device.

Several of the prior figures depict a number of guidewires that utilize tip member 30, which may take the form of a polymer tip. However, this need not be the case as other embodiments are contemplated. For example, FIG. 11 depicts guidewire 910 that includes a spring tip 930 that includes a coil 930a and a tip 930b, for example a solder ball tip 930b. A portion of coil 930a may be disposed along the exterior of tubular member 920, for example, along the outside of second section 920b of tubular member 920. Alternatively, coil 930a may abut tubular member 920. In general, spring tip 930 may function similarly to other spring tips commonly used in medical device designs.

Figure 12:
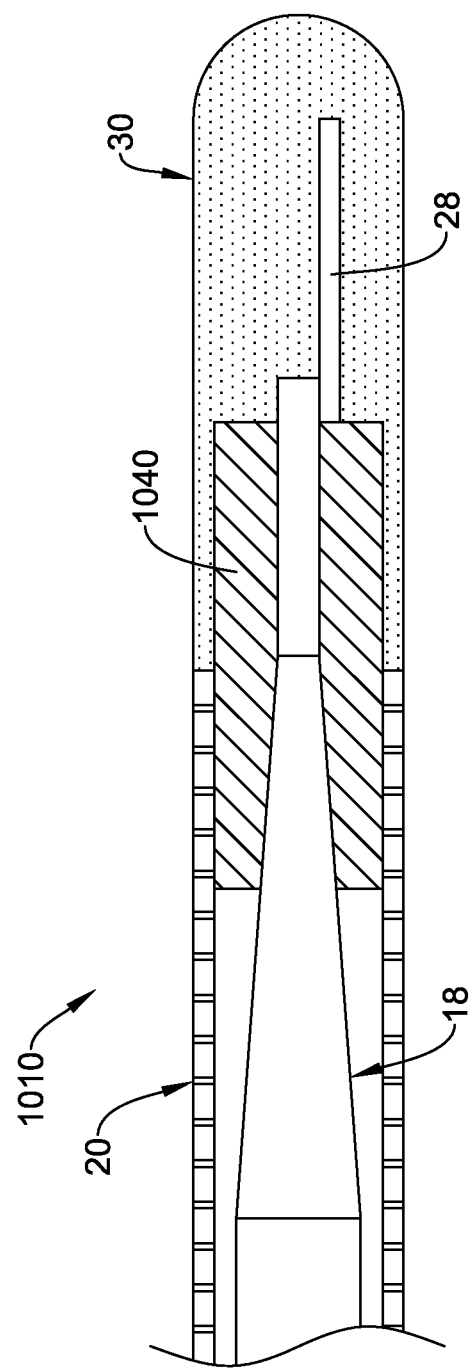
FIG. 12 is a partial cross-sectional view of another example medical device.

FIG. 12 illustrates another example guidewire 1010 that may be similar in form and function to any of the other guidewires disclosed herein except that an insert 1040 may be disposed between core wire 18 and tubular member 20. Insert 1040 (as well as other inserts disclosed herein) may function as an intermediate member like coil 32 or other structures described above and, consequently, it may provide a number of desirable features to guidewire 1010. For example, insert 1040 may increase the contact area between tubular member 20 and tip member 30. This may, for example, smooth the transfer of force along the length of guidewire 1010 and it may increase the kink resistance, for example, adjacent the junction of tubular member 20 and tip member 30. Additionally, insert 1040 may center the position of core wire 18 within tubular member 40 and insert may impede the flow of material (e.g., from tip member 30) proximally into tubular member 20 during the manufacturing of guidewire 1010.

In general, insert 1040 may be disposed within tubular member 20. In at least some embodiments, insert 1040 is disposed directly on core wire 18. Insert 1040 may extend distally beyond the distal end of tubular member 20 and overlap with tip member 30. Indeed, insert 1040 can be seen as overlapping with tubular member 20, core wire 18, and tip member 30. Tip member 30 may be directly bonded to insert 1040 using any suitable bonding strategy.

In at least some embodiments, insert 1040 may be a polymeric insert made from any of the polymers disclosed herein. For example, insert 1040 may include polyurethane. The shape and/or configuration of insert 1040 may also vary. For example, insert 1040 may have a generally cylindrical shape as illustrated in FIG. 12. Alternatively, other shapes may be utilized. For example, insert 1040' may have a star shape as illustrated in FIG. 13. Alternatively, insert 1040" may have a shape resembling a cylinder with a broken or uneven outer surface as illustrated in FIG. 14. It can be appreciated that any number of shapes may be utilized without departing from the spirit of the invention.

Figure 16:
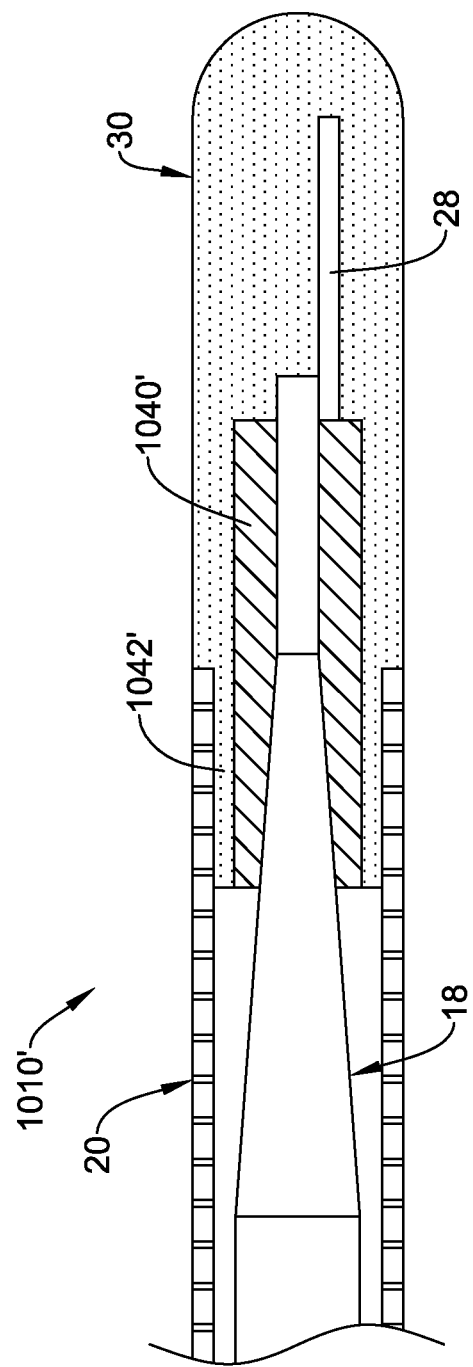
FIG. 16 is a partial cross-sectional view of another example medical device utilizing an insert like the ones illustrated in FIGS. 14-15.

As indicated above, it may be desirable to prevent the flow of material into tubular member 20 during the manufacturing of guidewire 1010 and/or other guidewires, for example through the use of insert 1040. In some instances, however, it may be desirable for material to migrate into tubular member 20. For example, allowing material such as polymeric material that may be used to construct tip member 30 to migrate or otherwise flow into tubular member 20 may further enhance the bond between tubular member 20 and tip member 30 and/or aid in transitioning the flexibility of guidewire 1010 between tubular member 20 and tip member 30. To aid in this, inserts like those shown in FIGS. 13-14 (e.g., inserts 1040'/1040" having a generally non-cylindrical shape) may provide a space or openings, for example openings 1042'/1042", for material to flow into tubular member 20 during the manufacture of guidewires like guidewire 1010. Indeed, FIG. 16 illustrates guidewire 1010' where opening 1042' is shown between tubular member 20 and insert 1040'. Because of opening 1042', the material of tip member 30 may be allowed to flow into opening 1042' between portions of insert 1040' and tubular member 20 during the manufacture of guidewire 1010'. This may help to ease the transition in flexibility between tubular member 20 and tip member 30. Although the reference number in FIG. 16 suggest the use of star shaped insert 1040' for having the material of tip member 30 migrate or flow along tubular member 20, it can be appreciated that essentially any suitable insert having a generally non-cylindrical shape may be utilized to achieve this configuration without departing from the spirit of the invention.

Figure 17:
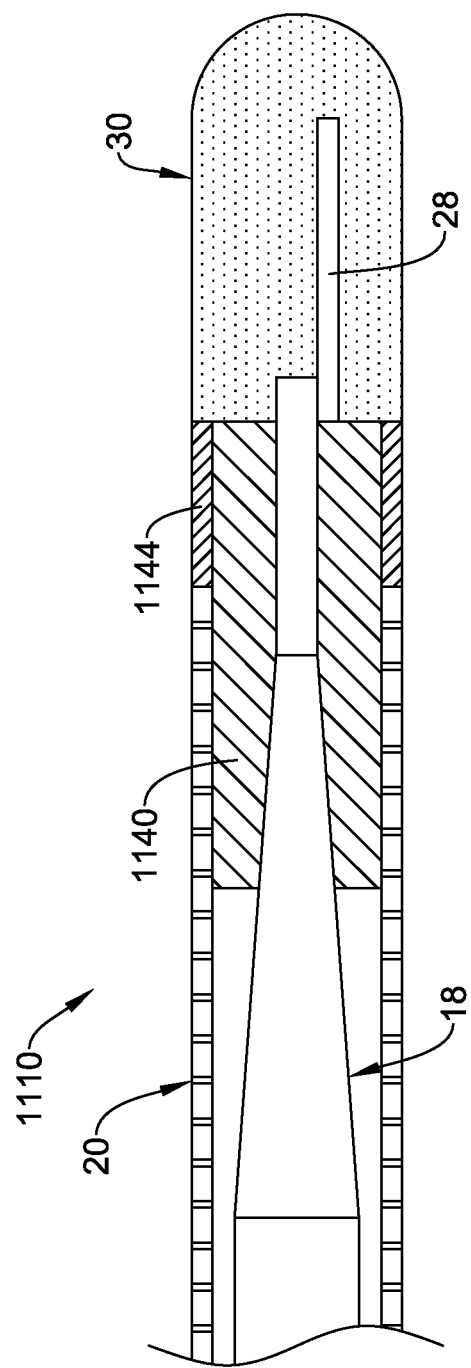
FIG. 17 is a partial cross-sectional view of another example medical device.

FIG. 17 illustrates another example guidewire 1110 that may be similar to other guidewires disclosed herein. Guidewire 1110 may include insert 1140 disposed within tubular member 20 and overlapping with tip member 30. At the distal end of tubular member 20 and disposed about insert 1140 may be a transition member 1144. Transition member 1144 may be made from the same material or a different material from tip member 30, insert 1140, or both. Transition member 1144 may provide guidewire 1110 with a number of desirable features and/or characteristics. For example, transition member 1114 may help guidewire 1110 have an even or uniform outer diameter across the transition between tubular member 20 and tip member 30.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical device, comprising:
an elongate core member, the core member having an outer surface, a central axis, and a solid cross-section from the outer surface to the central axis;
a tubular member disposed over a portion of the core member and bonded to the core member for permanent attachment of the tubular member to the core wire as provided for use in a medical procedure, the tubular member having a distal end;

wherein a plurality of slots are formed in the tubular member;
a polymeric tip member extending distally away from the distal end of the tubular member and including a proximal portion; and
an intermediate member disposed within the tubular member, wherein a portion of the intermediate member extends distally away from the distal end of the tubular member and overlaps with the proximal portion of the tip member.

2. The medical device of claim 1, wherein the intermediate member includes a coil.

3. The medical device of claim 1, wherein the intermediate member includes a portion of the tubular member.

4. The medical device of claim 1, wherein the intermediate member includes a second tubular member.

5. The medical device of claim 1, wherein the intermediate member includes a polymeric insert.

6. A medical device, comprising:
an elongate core member, the core member having a solid cross-section and being free of a lumen formed therein;
a tubular member disposed over a portion of the core member and bonded to the core member for permanent attachment of the tubular member to the core member as provided for use in a medical procedure, wherein a plurality of slots are formed in the tubular member;
wherein the tubular member includes a first section having a first outer diameter and a second section having a second outer diameter that is smaller than the first outer diameter;
wherein the first section of the tubular member is disposed proximally of the second section of the tubular member; and
a tip member coupled to the tubular member.

7. The medical device of claim 6, wherein the first section and the second section of the tubular member are formed from a single monolith of material.

8. The medical device of claim 6, wherein the tubular member includes a tapered section disposed between the first section and the second section that forms a smooth transition between the first outer diameter and the second outer diameter.

9. The medical device of claim 6, wherein the first section and the second section of the tubular member are formed from separate tubes that are attached to each other.

10. The medical device of claim 6, wherein a first section and the second section abut.

11. A medical device, comprising:
an elongate core member, the core member having a longitudinal axis, an outer surface, and a central axis;
wherein in a plane transverse to the longitudinal axis the core member is solid from the outer surface to the central axis;
a tubular member disposed over a portion of the core member and bonded to the core member for permanent attachment of the tubular member to the core member as provided for use in a medical procedure, wherein a plurality of slots are formed in the tubular member;
wherein the tubular member includes a first section having a first outer diameter and a second section having a second outer diameter that is smaller than the first outer diameter;
a tip member coupled to the tubular member; and
wherein the first section and the second section overlap.

12. The medical device of claim 6, wherein the tip member includes a polymer.

13. The medical device of claim 12, wherein a portion of the tip member is disposed along an outer surface of the tubular member.

14. The medical device of claim 12, wherein a portion of the tip member is disposed along an outer surface of the second section of the tubular member.

15. A guidewire, comprising:
an elongate non-tubular core wire, the core wire having a solid cross-section;
a tubular member disposed over a portion of the core wire and bonded to the core wire for permanent attachment of the tubular member to the core wire as provided for use in a medical procedure, the tubular member having a distal end;
wherein a plurality of slots are formed in the tubular member;
a tip member coupled to the distal end of the tubular member;
an intermediate member having a first portion disposed within the tubular member and a second portion overlapping with the tip member; and
wherein the intermediate member includes a portion of the tubular member.

16. A guidewire, comprising:
an elongate non-tubular core wire, the core wire having a solid cross-section;
a tubular member disposed over a portion of the core wire and bonded to the core wire for permanent attachment of the tubular member to the core wire as provided for use in a medical procedure, the tubular member having a distal end;
wherein a plurality of slots are formed in the tubular member;
a tip member coupled to the distal end of the tubular member;
an intermediate member having a first portion disposed within the tubular member and a second portion overlapping with the tip member; and
wherein the intermediate member includes a polymeric insert.

17. A guidewire, comprising:
an elongate non-tubular core wire, the core wire having a solid cross-section;
a tubular member disposed over a portion of the core wire and bonded to the core wire for permanent attachment of the tubular member to the core wire as provided for use in a medical procedure, the tubular member having a distal end;
wherein a plurality of slots are formed in the tubular member;
a tip member coupled to the distal end of the tubular member;
an intermediate member having a first portion disposed within the tubular member and a second portion overlapping with the tip member; and
wherein the tip member includes a polymer, a metal, or both a polymer and a metal.

18. A method for manufacturing a medical device, the method comprising the steps of:
providing an elongate core member, the core member having a solid cross-section and being free of a lumen formed therein;
disposing a tubular member over a portion of the core member, wherein a plurality of slots are formed in the tubular member, wherein the tubular member includes a first section having a first outer diameter and a second section having a second outer diameter that is smaller than the first outer diameter, wherein the first section of the tubular member is disposed proximally of the second section of the tubular member;

bonding the tubular member to the core member for permanent attachment of the tubular member to the core member for use in a medical procedure; and coupling a tip member to the tubular member.

* * * * *